United States Patent
Holub

(10) Patent No.: US 7,257,531 B2
(45) Date of Patent: Aug. 14, 2007

(54) SPEECH TO TEXT SYSTEM USING CONTROLLED VOCABULARY INDICES

(75) Inventor: John M. Holub, Hampshire, IL (US)

(73) Assignee: MEDCOM Information Systems, Inc., Hoffman Estates, IL (US)

( * ) Notice: Subject to any disclaimer, the term of this patent is extended or adjusted under 35 U.S.C. 154(b) by 1026 days.

(21) Appl. No.: 10/417,574

(22) Filed: Apr. 17, 2003

(65) Prior Publication Data

US 2004/0019482 A1    Jan. 29, 2004

Related U.S. Application Data

(60) Provisional application No. 60/373,924, filed on Apr. 19, 2002.

(51) Int. Cl.
    *G10L 15/26*    (2006.01)
(52) U.S. Cl. ............................ 704/235; 704/257
(58) Field of Classification Search .................. None
    See application file for complete search history.

(56) References Cited

U.S. PATENT DOCUMENTS

| | | | | |
|---|---|---|---|---|
| 5,799,273 A * | 8/1998 | Mitchell et al. | ............ | 704/235 |
| 5,799,276 A * | 8/1998 | Komissarchik et al. | ..... | 704/251 |
| 5,799,279 A * | 8/1998 | Gould et al. | ................ | 704/275 |
| 5,857,099 A * | 1/1999 | Mitchell et al. | ............. | 704/235 |
| 5,960,447 A * | 9/1999 | Holt et al. | ................... | 715/500 |
| 5,970,449 A * | 10/1999 | Alleva et al. | ................ | 704/235 |
| 6,088,671 A * | 7/2000 | Gould et al. | ................. | 704/235 |
| 6,122,614 A * | 9/2000 | Kahn et al. | ................... | 704/235 |
| 6,173,259 B1 * | 1/2001 | Bijl et al. | ..................... | 704/235 |
| 6,308,151 B1 * | 10/2001 | Smith | .......................... | 704/235 |
| 6,415,258 B1 * | 7/2002 | Reynar et al. | .............. | 704/275 |
| 6,457,031 B1 * | 9/2002 | Hanson | ...................... | 715/531 |

OTHER PUBLICATIONS

Berdy Medical Systems under the tradename SMARTCLINIC, information sheet regarding a CPR dictation system from internet website (see ww.berdymedical.com), dated Mar. 28, 2003.

* cited by examiner

*Primary Examiner*—David D. Knepper
(74) *Attorney, Agent, or Firm*—Pauley Peterson & Erickson

(57) ABSTRACT

A synthesis of automated speech recognition (voice to text) technology and a knowledge-based analysis of the concepts and contexts of the free text therefrom enable a directed-vocabulary look up index to be used in conjunction with the speech recognition technology thus enabling medical dictation to be transcribed in real time without elaborate training of the dictator or the speech recognition technology. Thus, caregivers can create and review Computer-Based Patient Records in the necessary timeframe consistent with good patient care. The Computer-Based Patient Records can be linked to other applications such as prescription cross checking, lab test results, payer regulations, etc.

20 Claims, 2 Drawing Sheets

US 7,257,531 B2

SPEECH TO TEXT SYSTEM USING CONTROLLED VOCABULARY INDICES

CROSS REFERENCE TO RELATED APPLICATION

This application claims the benefit of U.S. Provisional Application No. 60/373,924, filed 19 Apr. 2002.

DISCUSSION OF THE RELATED ART

Physicians are the key data collectors and generators within the health care system, creating a "visit note" to record an interaction with a patient. Manual data capture in the medical field has, in the past, been known to suffer shortcomings. Thus, Computer-Based Patient Record (CPR) data collection systems have been proposed to solve certain of the manual data capture shortcomings. Yet the known CPR systems are not being embraced by physicians. The ease of use of such systems is often cited as the major stumbling block to CPR adoption. Current CPR systems can be too complicated or too slow, or both, to be used effectively by many physicians. Some CPR systems may require that the time-constrained physicians learn separate operating methods or may require training of the computer systems to obtain adequate results from the system.

Known CPR systems fall into several categories including those that focus on capturing structured text through the use of pick lists, i.e. structured text displays, those that rely on free text generated by dictation through Automated Speech Recognition (ASR), and those that attempt to combine both methods. There can be limitations for each known system. Some known systems use a point-and-click input method for data entry into structured data computer forms. This system for the capture of the necessary data can be cumbersome and can slow office production. Some systems allow for dictation of free text and subsequent transcription. Some dictation systems' language recognition functions may require extensive training of the system by the physician for adequate accuracy. Other such systems may not offer real time voice-to-text conversion available to the physician. Further, the free text generated from such systems may essentially be just a word processing document and therefore may not be effectively or completely utilized, nor enable real-time decision support.

Thus, there remains a need for a CPR system which requires no training on the part of the physician and is fast, accurate, and conveniently usable, and does not arbitrarily restrict the vocabulary of the user. A system for generating visit notes which combines the ease of dictation with the ability to extract important medical terms from that dictated text to enable record standardization or further analysis of the data, or both, would also be desirable. Further, the system should desirably be fast enough to be real time or near real time (hereinafter simply referred to as "real time") in order to allow for review of the data intake and possible decision support during the time the patient is on-site with the physician. Further, the system should desirably effectively utilize the captured data to reduce costs within the medical care delivery system. These costs range from iatrogenic complications to requirements to complete a wide range of insurance documents for payment, to the time required to establish if a patient may be referred to a specialist, to the effort expended in ensuring that the pharmaceutical product recommended by the patient's provider is allowable by the health plan covering that patient. Time spent by healthcare personnel retrieving a patient's records and completed laboratory results should desirably be reduced. Errors in record generation and data retrieval should desirably be reduced. Unnecessary duplication of tests and procedures should desirably be eliminated.

SUMMARY OF THE INVENTION

The present invention provides solutions to the above discussed shortcomings in the known art. The present invention recognizes that, within a discipline, the vocabulary may be inherently limited and segmented into identifiable groupings. Thus, the present invention need not force artificial limits or segmentations on such vocabularies but only recognize and work with them. By analyzing the context of the vocabulary stream from a database of concept awareness and context recognition, vocabulary segmentation can be used in conjunction with Automated Speech Recognition (ASR) to create real time, accurate transcription without the need for additionally training the dictator or the ASR program. Further, by analyzing the free text coming from the ASR and predicting its context, the data may be transcribed and used in real time to enhance the functionality of the transcription process and desirably provide additional support services.

In one aspect of the present invention the data capture is effectively addressed by allowing the physician to dictate normally while the present invention creates a Computer-Based Patient Record (CPR) visit note. In other aspects of the present invention additional functionalities may manage the interpretation, feedback and processing of clinical, maintenance, and administrative duties and decision support.

Data capture is addressed through the combination of voice to text ASR in combination with a vocabulary segmentation system having a Text Interpreter function for at least one of word, phrase, and associated concept recognition; a Predictive Vocabulary Controller function for predicting the context of at least one of the words, phrases, and concepts, and a Vocabulary Segmentation Controller to provide vocabulary segmentation to the ASR for speed and accuracy of transcription.

It is noted, without limitation to the present invention, that adequately robust voice to free text (ASR) systems which may be used in conjunction with the present invention are commercially available. These commercial voice to free text systems may then be used within the present invention to focus on the specific vocabulary requirements of an industry, such as medical treatment.

The present invention can eliminate training of ASR systems by creating a closed-loop system for accurately and quickly converting speech to text by changing sound files to text, dynamically analyzing the text to predict the context of the dictation, and based on the predicted context, providing restricted vocabulary lists, or indices, to the sound file converter of the ASR to further speed sound file conversion.

Thus, according to certain aspects of the present invention, after voice to free text conversion, a Text Interpreter engine operates to recognize vocabulary meaning, or relevance. A Predictive Vocabulary Controller then predicts a context for the dictation stream and selects an appropriate "restricted" vocabulary index, or indices, of restricted proportion or size adequate for the predicted context of the dictation when compared to a more general vocabulary. A Vocabulary Segmentation Controller then interfaces the selected restricted vocabulary index with the ASR to speed sound file to text file conversion and provide real time transcription. The evaluation, or analysis, occurs dynamically so that the meaning and context of the text data stream are continually evaluated and predicted and restricted indices are continually updated for use with the ASR.

Using the medical industry as an example, patient record generation, e.g., a visit note, generally follows a set pattern. For example the so-called S.O.A.P. record format of Subjective (patient input), Objective (physician observation), Assessment (diagnosis), and Plan (treatment recommendation) segments may be used as the pattern. Each segment of the S.O.A.P. record format will have a characteristic vocabulary. Within the context of each S.O.A.P. segment a variety of well defined vocabulary subcategories, or "subvocabulary segments" will exist. For example, the context of the Assessment segment will have a characteristic vocabulary. An assessment of "cardiac disease" will denote another context with a characteristic, and more specific, subvocabulary of fewer words. A specific form or type of cardiac disease will have a further refined subvocabulary. While it is considered likely that most subvocabularies will have a reduced vocabulary from a preceding more generic vocabulary index, it will be appreciated that refinement of the vocabulary list to the specific context of the dictation does not necessarily entail a reduction of vocabulary from an immediately preceding index.

Once the data is captured electronically it can be cross-referenced or compared, again in real time, by an additional application or suite of applications to other relevant data to ensure further utilization of the data. For example, within the medical field once the data is captured electronically it can be cross-referenced or compared by a physician support suite of applications to other available patient data and to clinical and economic requirements necessary to ensure effective patient treatment and reimbursement of all concerned parties. Further, the data may be applied to precondition the present invention for obtaining other visit notes for the same patient in the future. Also, for example, parts of the dictation may be extracted and ordered to supply the physician or patient with, e.g., a set format visit note or a summary of the visit note, including specific listings for medications, allergies, diagnosis, orders, laboratory results, etc. Because of the real time capability of the dictation portion of the present invention, some or all analysis may occur quickly enough to be accomplished during the patient visit.

The present invention thus provides accurate capture of voice files, rapid interpretation and effective usability without the need for training an ASR and without artificially restricting data entry means or vocabularies.

DETAILED DESCRIPTION OF THE PRESENTLY PREFERRED EMBODIMENTS

Discussion of the modules or parts of the exemplary embodiment will be given herein with respect to specific functional tasks or task groupings that are in some cases arbitrarily assigned to the specific modules for explanatory purposes. It will be appreciated by the person having ordinary skill in the art that a system according to the present invention may be arranged in a variety of ways, or that functional tasks may be grouped according to other nomenclature or architecture than is used herein without doing violence to the spirit of the present invention.

Figure 1:
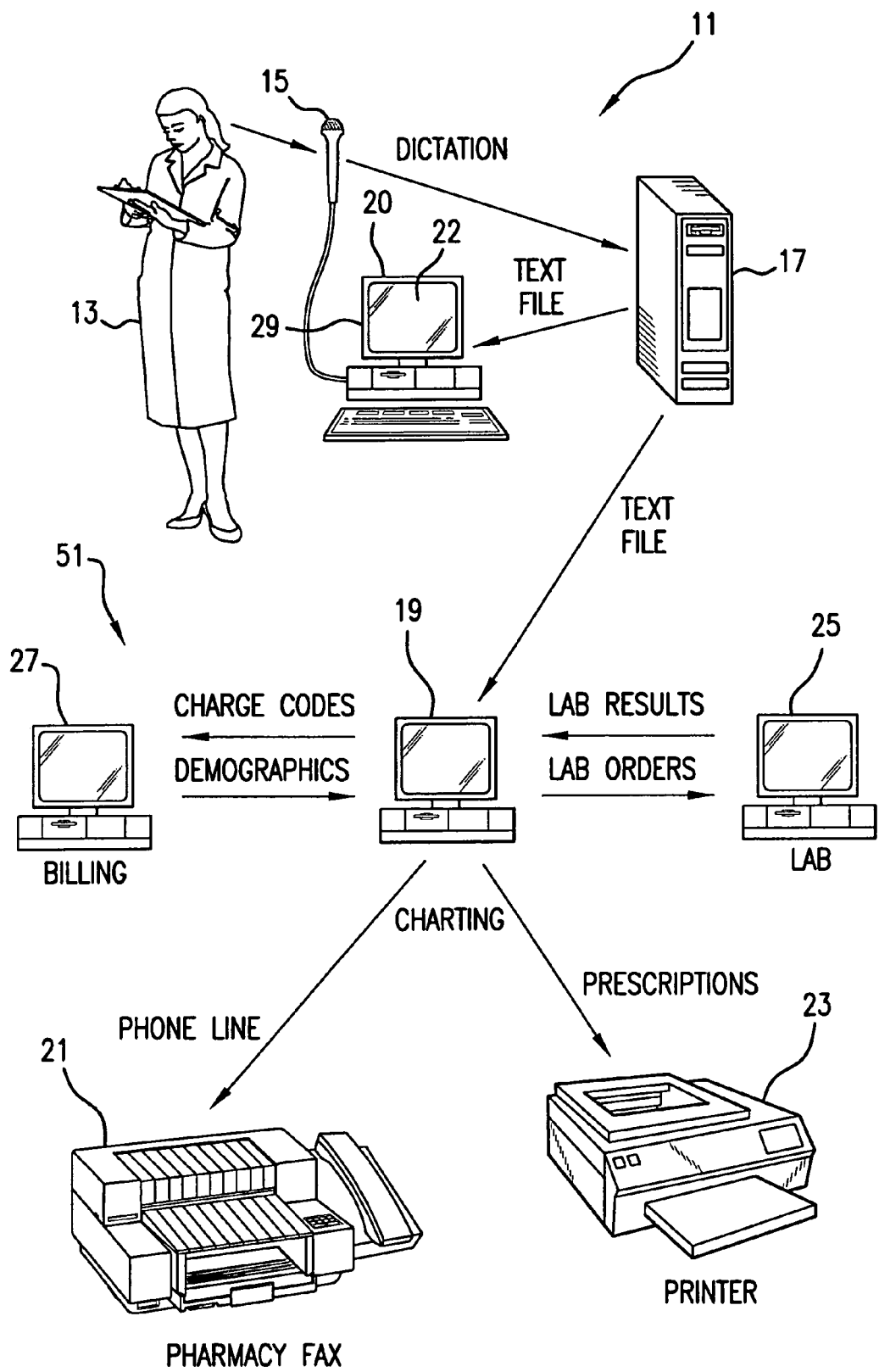
FIG. 1 is a schematic illustration of one embodiment of the present invention.

As seen in FIG. 1, an exemplary aspect of the present invention 11 will permit a user, here a physician or other caregiver, 13 to provide dictation into a microphone 15. Physician dictation is then initially received and processed by electronic speech conversion means 17 such as a computer running an Automated Speech Recognition (ASR) application, e.g., such as adequately robust commercial voice to free text systems which may include DRAGON NATURALLY SPEAKING from ScanSoft Inc. of Peabody, Mass., or IBM VIA VOICE from International Business Machines Corporation (IBM) of Armonk, N.Y. These commercial voice to free text systems may then be used within the present invention to focus on the specific vocabulary requirements of an industry, such as medical treatment. The electronic speech conversion means 17 then matches the sound files of recorded speech into text. As indicated in the figure, the microphone 15 may be remote from the speech conversion means 17 and connected by wired or wireless transmission means to the electronic speech conversion means 17, or the microphone 15 may be attached directly to the electronic speech conversion means 17.

A Display Control 20 forms the physician's user interface. The Display Control 20 may be in the form of a personal computer, a personal digital assistant, or the like with specialized software and a microphone. The Display Control 20 permits the user to re-dictate for editing or making corrections to the visit note. The Display Control 20 may be a touch screen monitor 22 that will display the dictated text, alerts, etc. The physician 13 can use the touch screen monitor 22 to override certain automated processes such as diagnosis and procedure coding. There are occasions where more than one correct code (e.g., Current Procedural Terminology (CPT) or International Classification of Diseases (ICD)) can be chosen. The physician 13 may not be able to remember all of the choices and can select the most appropriate from a displayed list or may have entered codes verified for correctness by the system. The physician 13 may also want to chose a personalized vocabulary set for certain dictation needs. It will be possible for the physician to validate and, if necessary, correct or edit the dictated visit note before the patient leaves the office. A Navigation/Data/Command switch function (not shown) will permit the physician 13 to have full interactive control of the Computer-Based Patient Record (CPR) process so the physician 13 can use verbal or touch screen commands, or both, that provide navigation commands to the application or the operating system, or both, that are not to be a part of the text based document. The physician 13 can call for other screens such as the previous patient encounters (office visits, physicals, etc.) or page up commands, redictation, or the like.

Figure 2:
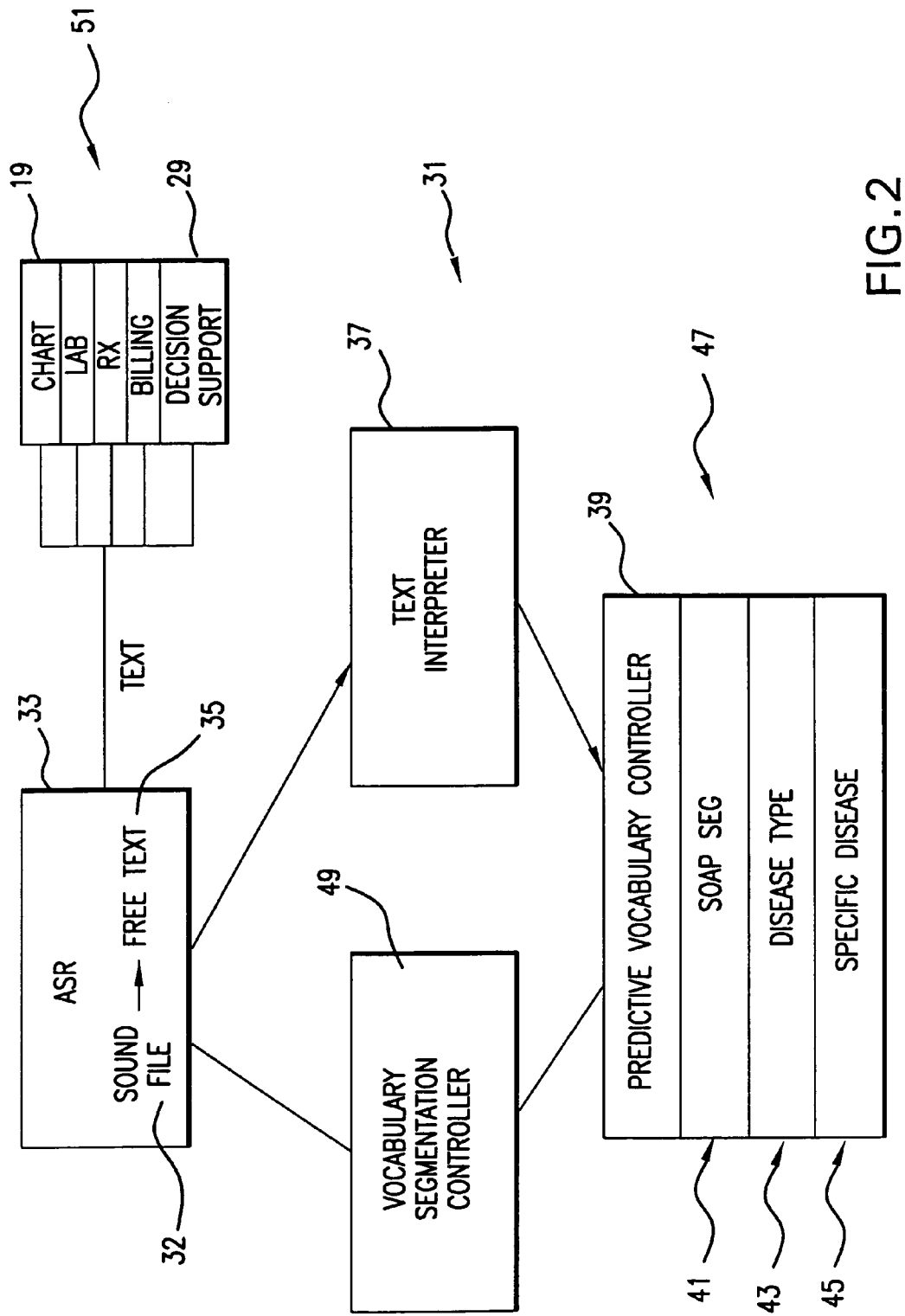
FIG. 2 is a block diagram of the speech recognition and vocabulary indices controller aspect of one embodiment of the present invention.

Referencing FIG. 2, in order to provide real time transcription and support services, the present invention utilizes a knowledge of the specialized and restricted vocabulary of the medical field. It will be appreciated that the present invention need not artificially limit the speech of the physician but merely utilizes a knowledge of medical vocabulary to manage and speed dictation. As further explained below, because of the speed of text conversion, all physician support services of the present invention may be available in real time, as is considered necessary for best practice of patient care.

A closed loop control 31 starts with the conversion of a sound file 32 to free text 35 by an ASR 33. Next the text words are dynamically analyzed for meaning or importance by the Text Interpreter 37. Once, or if, the word meaning or importance is recognized, the text 35 is then operated on by a Predictive Vocabulary Controller 39 to predict the context, i.e., where the physician is in the dictation of the visit note, by comparing the vocabulary stream used against accepted vocabulary usage, word groupings, or protocols used by physicians. The Predictive Vocabulary Controller 39 then determines the restricted vocabulary lists, i.e., index or indices 41, 43, 45, of the vocabulary library 47 that will most likely apply to the dictation of the physician at that moment.

For example, when the physician states "Assessment" the vocabulary can be segmented to a diagnosis vocabulary index. As shown, a specific assessment of "cardiac disease" will denote another context with a characteristic, and more specific, restricted, or refined, subvocabulary index of fewer words. An assessment of a specific form or type of cardiac disease will have a further refined subvocabulary. The Predictive Vocabulary Controller 39 then informs the Vocabulary Segmentation Controller 49, which is an interface or controller operably connected to the ASR 33, which indices are selected for priority of use with the ASR 33. The Vocabulary Segmentation Controller 49 then manages the use of the selected vocabulary indices in conjunction with the appropriate sound file-to-text matching of the ASR conversion. This vocabulary segmentation minimizes the possible words that the speech recognition function will have to sort through, enabling real time use of the present invention.

The Text Interpreter 37 performs the text analysis by accepting the natural language text, i.e., free text, sentences from the ASR 33 and parsing and assembling the text into relevant "concepts", or key types or categories of information. The Text Interpreter 37 first breaks each sentence into individual words and then may combine the words into phrases. Each word can be treated as a weighted token and the parsing can eliminate the irrelevant, or non-indicative, words of the natural language structure. For example, in the text: "An assessment of the patient is as follows," words irrelevant to data evaluation such as "an" and "the" may be eliminated from use as tokens by the parser module. Each word and phrase may be compared to concept indices in one or more vocabulary databases, e.g. vocabulary lists as supplied by the system and as developed by the user. The system may provide the option of having the user vocabulary take precedence over the system-supplied vocabulary in this process. To identify concept phrases, the parser may also look for indicators like parentheses, punctuation, and the like to decide where clauses begin and end. The parser can also look for terms that represent negation (not, isn't, didn't, although, etc.), as well as "and", "or", and other Boolean type terms which will be used to identify the concepts. Various techniques such as grammar matching, lattices, partial lattices, etc., for accomplishing the tasks of the Text Interpreter 37 are available and considered within the skill of the person having ordinary skill in the art. A concept expander may also be used for receiving the parsed natural language (free text) and obtaining additional terms synonymous or analogous to the words and phrases to expand the concept search. Various techniques such as thesauri, dictionaries, term expansion, stemming, phrase generation, and the like are available to accomplish this expansion and are considered within the skill of the person having ordinary skill in the art. A large database of word and phrase synonymies for identifying concepts within the medical industry vocabulary has already been built by the WELFORD CHART NOTES charting program from Welford Medical Computing, Inc., of Rockford, Ill. The Text Interpreter 37 may then identify relevant words and phrases by concept numbers.

The Predictive Vocabulary Controller 39 can then evaluate the concepts currently in the dictation stream to provide a context prediction, or determination, e.g., determining the most likely segment of the visit note data entry process (e.g., S.O.A.P. segment) which a physician is creating. The Predictive Vocabulary Controller 39 can then select a vocabulary index 41, 43, 45 having a refined or specific vocabulary list, often with a restricted number of words, most appropriate to that segment of the visit note data entry process. The Predictive Vocabulary Controller 39 can then direct the Vocabulary Segmentation Controller 49 to utilize the selected vocabulary index in its interaction with the ASR 33. Thus the ASR wave to text conversion can operate with smaller vocabulary list matching. Through the use of appropriately restricted or refined vocabulary indices, and prediction of which indices will be needed to generate the transcription text data, real time speed and accuracy of transcription and additional data manipulation may be obtained with minimal software and hardware expenditures and eliminate the drudgery of training an ASR application.

Additional tasks such as visit note construction or other analysis applications may utilize the concept identification to aid in their task accomplishment. A Physician Support Suite of applications 51 can thus be provided by aspects of the present invention to fully integrate the advantages thereof in real time patient and practice support. For example the text, preferably once analyzed for concept or context, or both, may be operated upon to provide a CPR display 19 and a variety of physician support clinical and administrative services including drug ordering 21, 23, lab work integration 25, billing management 27, and physician decision support and validation 29 through commercially known or later developed systems. For example, the previously mentioned charting application, WELFORD CHART NOTES, is a full featured application for creating and utilizing a CPR as well as providing many physician support services such as clinical duties including prescription checking warnings including: allergies, interactions, precautions, contraindications, inappropriate dosages, and formulary violations; and lab results analysis, rules reminders, and other decision support functions, as well as maintenance duties including automated patient file updates for warnings, corrections, notations, and the like; and administrative duties including diagnosis and procedure code entry validation or suggestions or other clinical code charting and automated billing functions.

The Physician Support Suite of applications 51 may include a variety of applications. The inventors contemplate integration of one or more types of support applications, exemplified by the following commercially available applications, into the functional whole of an embodiment of the present invention. A lab management application, MEDCOM LAB MANAGER, from Medcom Information Systems, Inc., of Hoffman Estates, Ill., may be integrated for test ordering and results reporting. MEDCOM LAB MANAGER is a complete laboratory information system that may connect to all the analytical instruments in the clinical laboratory and produce a consolidated report for the physician. A medical practice accounts receivable application, EDIMIS PRACTICE MANAGER, which is supplied by Edimis, Inc., of Collierville, Tenn., may be integrated for billing in an independent medical practice. Similarly, a billing application, such as HOSPITAL MANAGER or CLINIC MANAGER, which are supplied by Integrated Systems Development Inc. of Aurora, Colo., may be integrated for inpatient and outpatient hospital billing as well as by medical practices owned or supported by hospitals.

The person having ordinary skill in the art will appreciate that there has been described an exemplary embodiment. It will recognized that many of the functionalities described herein can be accomplished by a variety of hardware, firmware and software methods and apparatus within the scope of the present invention. Having thus described the present invention, it will be appreciated that many variations thereon will occur to the artisan upon an understanding of the present invention, which is therefore to be limited only by the appended claims.

I claim:

1. An Automated Speech Recognition system for taking dictation wherein the dictation has one or more recognizable contexts, comprising:
   a) means for capturing a first voice input of a dictator at a first time;
   b) means for changing the first voice input into a first sound file;
   c) means for comparing the first sound file to a first vocabulary list to make text;
   d) means for analyzing the text to predict a context of the text;
   e) means for selecting a second vocabulary list of refined word choice from the first vocabulary list based on the context of the text;
   f) means for capturing a second voice input of a dictator at a second time;
   g) means for changing the second voice input into a second sound file; and
   h) means for comparing the second sound file to the second vocabulary list to make text.

2. The Automated Speech Recognition system according to claim 1 wherein the means for analyzing the text includes means for dynamically analyzing the text.

3. The Automated Speech Recognition system according to claim 1 further comprising means for extracting and ordering the text in different formats from the dictation.

4. The Automated Speech Recognition system according to claim 1 wherein the means for analyzing includes means for recognizing words and predicting the context of the words.

5. The Automated Speech Recognition system according to claim 1 wherein the means for analyzing includes means for recognizing phrases and predicting the context of the phrases.

6. The Automated Speech Recognition system according to claim 1 wherein the means for analyzing includes means for recognizing words and associating the words with concepts, and predicting the context of the concepts.

7. The Automated Speech Recognition system according to claim 1 wherein the means for analyzing includes means for recognizing phrases and associating the phrases with concepts, and predicting the context of the concepts.

8. The Automated Speech Recognition system according to claim 1 further including a support suite of applications for an addition of at least one of a clinical, maintenance, and administrative duty functionality.

9. A Computer-Based Patient Record system for taking dictation wherein the dictation has one or more recognizable contexts, comprising:
   a) means for capturing a first voice input of a dictator at a first time;
   b) means for changing the first voice input into a first sound file;
   c) means for comparing the first sound file to a first vocabulary list to make text;
   d) means for analyzing the text to predict a context of the text;
   e) means for selecting a second vocabulary list of refined word choice from the first vocabulary list based on the context of the text;
   f) means for capturing a second voice input of a dictator at a second time;
   g) means for changing the second voice input into a second sound file;
   h) means for comparing the second sound file to the second vocabulary list to make text; and
   i) means for constructing a patient visit note with at least a portion of the text.

10. The Computer-Based Patient Record system according to claim 9 wherein the means for analyzing includes means for recognizing at least one of words or phrases and predicting the context of the words or phrases.

11. The Computer-Based Patient Record system according to claim 9 wherein the means for analyzing includes means for recognizing at least one of words or phrases and associating the words or phrases with concepts, and predicting the context of the concepts.

12. The Computer-Based Patient Record system according to claim 9 further including a support suite of applications for the addition of at least one clinical, maintenance and administrative duty functionality.

13. The Computer-Based Patient Record system according to claim 12 wherein the clinical duties include at least one of prescription checking warnings including: allergies, interactions, precautions, contraindications, inappropriate dosages, and formulary violations, and lab results analysis.

14. The Computer-Based Patient Record system according to claim 12 wherein the maintenance duties include automated patient file updates.

15. The Computer-Based Patient Record system according to claim 12 wherein the administrative duties include at least one of a diagnosis and procedure coding duty and an automated billing duty.

16. The Computer-Based Patient Record system according to claim 9 further including means for editing the patient visit note.

17. A method for taking dictation wherein the dictation has one or more recognizable contexts, comprising:
   a) capturing a first voice input of a dictator at a first time;
   b) changing the first voice input into a first sound file;
   c) comparing the first sound file to a first vocabulary list to make text;
   d) analyzing the text to predict a context of the text;
   e) selecting a second vocabulary list of refined word choice from the first vocabulary list based on the context of the text;
   f) capturing a second voice input of a dictator at a second time;
   g) changing the second voice input into a second sound file; and
   h) comparing the second sound file to the second vocabulary list to make text.

18. The method for taking dictation according to claim 17 further comprising constructing a patient visit note with at least a portion of the text.

19. The method for taking dictation according to claim 18 further comprising analyzing the patient visit note to provide additional physician support services.

20. The method for taking dictation according to claim 17 further comprising extracting and ordering at least parts of the text to create documents in formats other than that of the dictation.

* * * * *